United States Patent [19]

Wood et al.

[11] Patent Number: 4,957,346
[45] Date of Patent: Sep. 18, 1990

[54] ILLUMINATION SYSTEM FOR PORTABLE COLOR IMAGER BORESCOPE

[75] Inventors: Robert J. Wood; Earl H. Slee, both of Syracuse; Gregory E. Pasik, Auburn; Michael J. Pileski, Warners, all of N.Y.

[73] Assignee: Welch Allyn, Inc., Skaneateles Falls, N.Y.

[21] Appl. No.: 417,555

[22] Filed: Oct. 6, 1989

[51] Int. Cl.$^5$ ............................................. G02B 23/26
[52] U.S. Cl. ................................. 350/96.26; 358/98; 358/100
[58] Field of Search ............... 358/98, 100; 350/96.26, 350/96.25, 96.24; 128/4–8

[56] References Cited

U.S. PATENT DOCUMENTS 4,562,831  1/1986  Murakoshi et al. .................... 358/98
4,769,693  9/1988  Kato .................................... 358/98

Primary Examiner—William L. Sikes
Assistant Examiner—John Ngo
Attorney, Agent, or Firm—Wall and Roehrig

[57] ABSTRACT

This invention involves a lighting system for a portable borescope in which the light is turned on and off at video frequencies and the duration of actuation is controlled in relation to the illumination picked up by the video imager in the distal end of the borescope insertion tube. By turning off the lamp for a significant portion of the duty cycle, a significant amount of power is saved, allowing use of the system in a battery operated borescope.

9 Claims, 3 Drawing Sheets

ILLUMINATION SYSTEM FOR PORTABLE COLOR IMAGER BORESCOPE

BACKGROUND OF THE INVENTION

This invention relates generally to a borescope or endoscope for providing full color video images of inaccessible objects of the type having an elongated insertion tube for passage into remote cavities and more particularly to an illumination system for portable, compact, battery-operated borescopes.

A borescope is generally characterized as an elongated flexible insertion tube with a viewing head at the distal end and a control and processing section at the proximal end. The control section has generally included one or two pairs of control cables extending from a bendable tube section adjacent the distal end through the remainder of the insertion tube to connect to the steering control mechanism in the control section. Various devices have been provided in the prior art for realizing a full color video picture of a target situated within a remote cavity. These devices have gradually improved over time to where today most devices of this type employ an external light source conveyed to the image viewing head by fiber optic bundles, together with a solid state image sensor and lens system positioned in the distal end of the insertion tube operatively connected to an external video processing system and standard television format display.

Endoscope/borescope systems of this general type have been disclosed in various patents owned by a common assignee of the present applicant, such as U.S. Pat. No. 4,253,447 to Moore et al.; U.S. Pat. No. 4,261,344 to Moore et al; and U.S. Pat. No. 4,491,865 to Danna et al. Another endoscope system is shown in U.S. Pat. No. 4,621,618 to Omagari, which describes a central control/display/light station, and a drive motor body for the insertable endoscope portion. The central control has a joystick actuated motor drive circuit for the motor mounted adjacent to and which manipulates the wire controlled bendable section of the insertion tube. This rather large cumbersome system requires a paramedic to handle the endoscope while the doctor operates the device from the control station. Also, the apparatus obviously is not portable.

As part of the need for greater flexibility and portability, the control of the steering function of a borescope has had to be simplified and improved both from an operating, as well as adjustability and maintenance viewpoint. In addition, the illumination system of the portable borescope has to be able to operate for extended periods of time without access to commercial power to provide optimum illumination of the object being viewed. As is well known in the art, the greater the power demands of a device, the larger the batteries that are required to power the unit and the more cumbersome the unit becomes in terms of portability and access to areas of restricted space. One of the major power consuming devices in a borescope/endoscope system is the lamp used to provide illumination through the fiber optic bundles to the viewing head for illuminating the object to be viewed. Generally speaking, the longer the insertion tube and the greater the distance from the viewing head to the object to be viewed, the greater the light output that is required, and the greater the power consumption and hence battery drain. Frequently, lamps of several hundred watt output are required to properly illuminate an object to be viewed, which poses a very significant drain on a small, compact battery pack for a portable borescope system.

OBJECTS AND SUMMARY OF THE INVENTION

It is therefore an object of the present invention to provide a lighting system for a compact, portable borescope that avoids the drawbacks of the prior art.

It is another object of the invention to provide a highly efficient lighting system for borescopes that requires a minimum amount of battery power.

It is another object of the present invention to provide a lighting system capable of illuminating an object at a maximum viewing distance, but which is automatically turned off a substantial portion of the time when lesser illumination is required.

It is another object of the present invention to provide a lighting system that is easy to install, service and maintain.

It is a still further object of the present invention to provide an illuminating system in which the lamp can be simply and easily replaced.

It is a still further object of the present invention to provide a lamp control system that will permit utilization of a variety of high efficiency lamps of different types.

It is a still further object of the present invention to provide an illuminating system in which the lamp control system actually interrupts the power to the lamp during that portion of each cycle of excitation that is not needed to illuminate the object to be viewed.

These and other and further objects and features of the invention will be more fully understood from the ensuing detailed description of the preferred embodiment of the invention, which description should be read in conjunction with the accompanying drawings.

DETAILED DESCRIPTION OF THE PREFERRED EMBODIMENT

Figure 1:
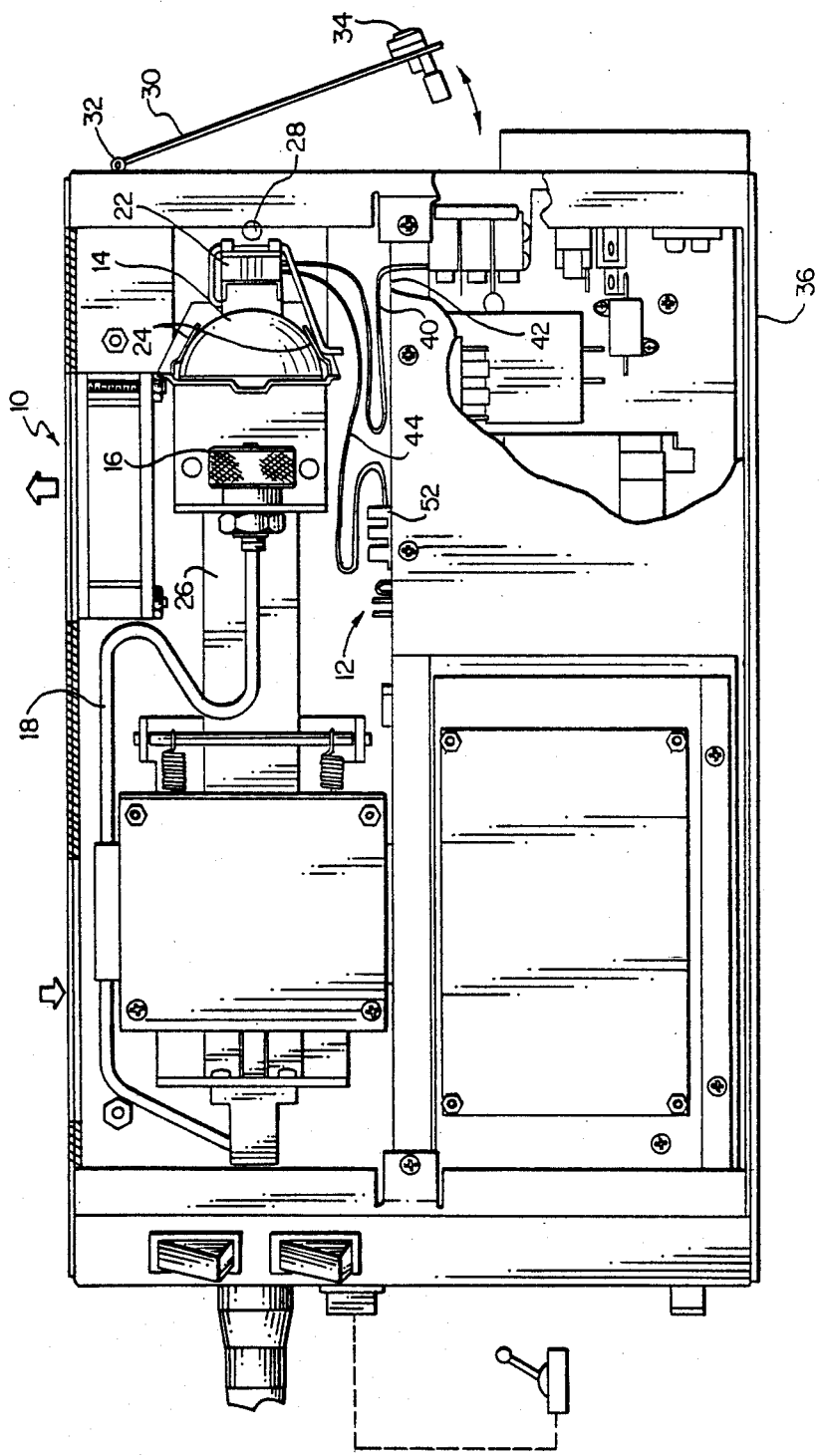
FIG. 1 is a top plan view, partially broken away of the light system according to the present invention.

Referring now to FIG. 1, the illuminating system 10 for a borescope includes a light dimmer board 12 for controlling the lamp 14 which is mounted to project illumination into a fiber optic cable termination 16 which feeds light into the fiber optic cable 18 which extends through the insertion tube to the viewing head at the distal end of the insertion tube to illuminate the object to be viewed. The lamp 14 is mounted in light assembly 20, which includes the socket 22 which receives the contacts from the base portion of the lamp and a pair of spring clamps 24 for holding the lamp in proper alignment with the fiber optic cable termination 16 so that the illumination from the lamp 14 is projected into the fiber optic cable 18.

Figure 2:
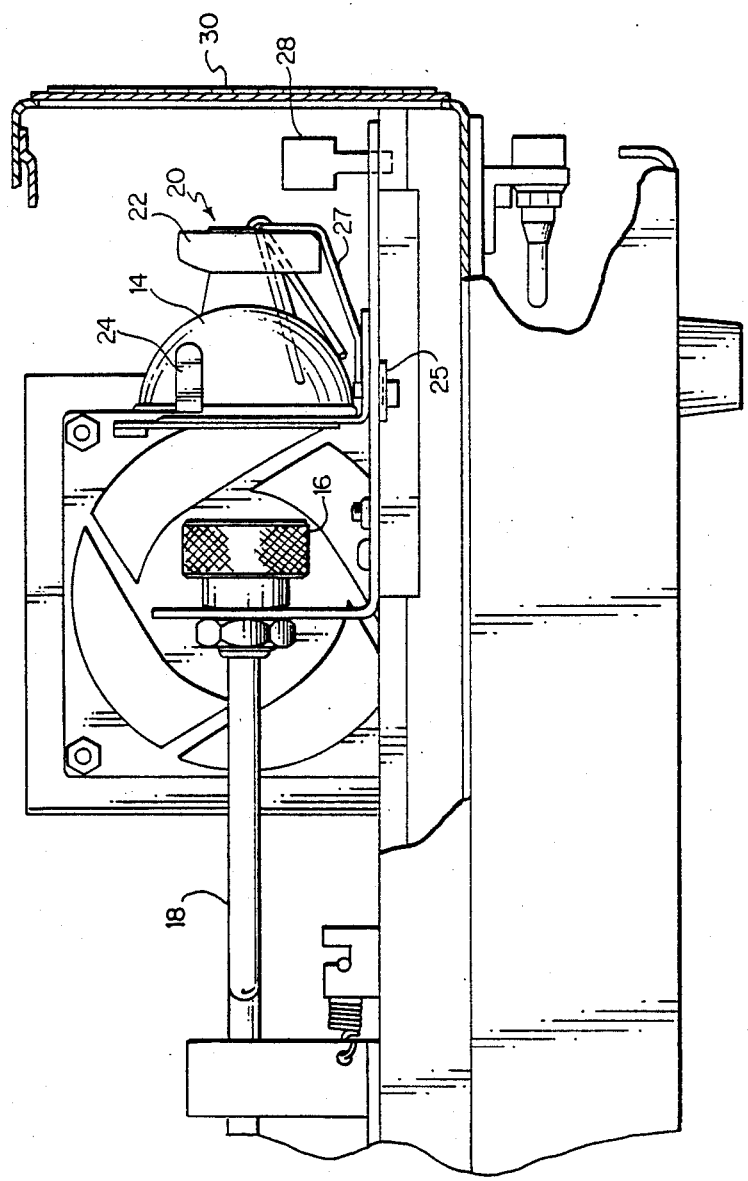
FIG. 2 is a side elevation of the lamp portion of the apparatus shown in FIG. 1.

The entire light assembly 20 is mounted on a bracket 25 which is slidably mounted on T-track 26 which normally is of a plastic material such as Teflon. The light assembly 20 is held in the desired position on the track 26 by latch mechanism 28, which is a spring loaded pin which extends from the top of bracket 25 into a mating section of the frame to secure the light in the proper position on the T-track 26. As may be seen in FIGS. 1 and 2, a door 30 hinged at 32 with a latch at 34 for closure thereof is provided in the housing 36 for the device to permit ready access to the light assembly 20.

For service of the lamp 14, door 30 is opened, the latch 28 is extended and the light assembly 20 is pulled outwardly from the housing 36 by sliding bracket 25 along T-track 26. Once outside the housing, the lamp can then be simply and easily removed vertically by sliding out of the springs 24 and socket 22 for cleaning and/or replacement as required. An ejector lever 27 is provided to assist in lamp removal.

Socket 22 receives the prongs of the light 14 in spaced apart contacts, as is common in the industry, with one of the contacts being connected to conductor 40 which is connected directly to the twelve volt source in a power supply through a shielded partition 42 which will limit as much as possible interference radiated from the power supply as the power to the lamp 14 is turned on and off. The other contact in the socket 22 is connected to the circuit board 12, by wire 44, as will be explained in detail in reference to FIG. 3. Fiber optic cable 18 and cables 44 and 40 have suitable slack therein for extension of the light assembly 20 when the assembly is pulled out on the T-track to remove or service the lamp 14.

Figure 3:
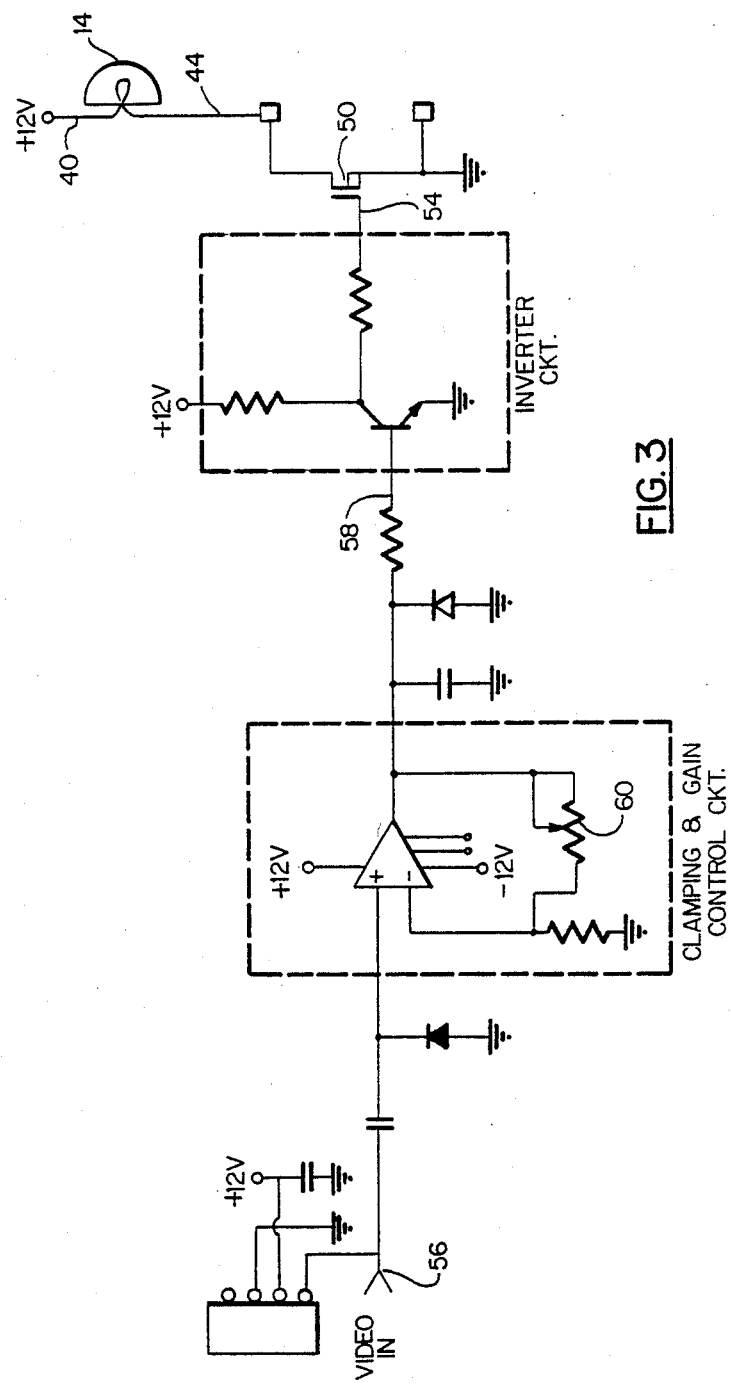
FIG. 3 is a schematic diagram of the lamp control circuit according to the present invention.

Referring now to FIG. 3, there is shown the dimmer circuit for controlling the light output of the lamp 14 in accordance with the video pick up requirements of the image detection circuit at the distal end of the insertion tube. As may be seen at the right hand end of FIG. 3, the lamp 14 is connected at one side directly to the +12 from the power supply through the lead 40 which, as may be seen in FIG. 1, is a very direct, short connection. The other side of the lamp 14 is connected to ground through a power Mosfet 50 which is mounted in a heat sink 52, the outline of which is seen in FIG. 1 on the central partition of the housing 36. The power Mosfet 50 has a threshold voltage above which it will conduct and below which it will not. Thus, it acts in effect as a switch which is open until a threshold voltage is reached at point 54 at which time the Mosfet conducts and connects the lamp 14 to ground and allows the lamp to be illuminated.

The voltage at 54 is controlled in accordance with the output from the video processor, which is proportional to the amount of light picked up by the video detector in the image sensor at the distal end of the insertion tube. The video output from the video processor is connected to the dimmer control board at 56. The signal from 56 is fed through a clamping and gain control circuit to develop a video rate signal at 58 which is then fed through an inverter circuit to cause the voltage at 54 to move in a direction opposite to the voltage at 58.

Potentiometer 60 may be adjusted to set a minimum floor to which the video signal is applied to turn on the lamp 14. This effectively provides adjustment for the base level of target illumination for the light system.

Thus, in operation, as the light intensity at the video pickup increases and the "video-in" signal at 56 increases, the voltage at 58 will increase. This in turn, will cause the voltage at 54 to decrease, dropping the control voltage on the Mosfet below the threshold voltage and turning off the lamp 14. As the light reflected from the image, as received by the video detector, decreases, the signal at 56 decreases, causing the voltage at 58 to decrease, which in turn, causes the voltage at 54 to increase. When it exceeds the threshold, it will turn the lamp 14 back on by completing the circuit from the +12 volts through the lamp to ground. As may be seen, this is done at video frequencies in accordance with the direct feedback loop such that the lamp is activated only for that portion of the cycle which is needed to produce enough illumination to properly illuminate the object to be viewed. Since the light is turned on and off at video frequency, the human eye will only see a brighter or dimmer light as the case may be. The TV image will appear only illuminated in a steady full color light.

In use, a borescope generally is inserted into a closed cavity with very little, if any, ambient light available. The light needed to properly illuminate the object to be viewed must be supplied from the fiber optic cable 18 at the distal end of the insertion tube. The amount of this light required to properly illuminate the object so that the video pickup can see it will vary, depending upon the distance the video pickup and the fiber optic bundle in the distal end of the insertion tube are from the object to be viewed. Generally, as the viewing head of the insertion tube is positioned closer to the object to be viewed, less light output is required from the lamp 14, and as a 10 result the lamp 14 may be turned off a greater percentage of the operating time. Since most inspection operations are done at relatively close range, this allows the lamp to be turned off a significant amount of time during operation of the device and thus, conserves on battery power.

Typically, the lamp 14 is a lamp in the one hundred to three hundred watt range, depending upon the particular instrument involved, and as such, consumes a very considerable amount of electrical power. In the preferred embodiment herein, the lamp 14 is a seventy-five watt halogen lamp which draws approximately eight amps at twelve volts and which is therefore a significant power drain on the battery pack of a portable borescope system. By turning on the lamp 14, only the amount of time needed to satisfy the requirements of the video imager pickup unit, a very substantial amount of battery power can be conserved. It has been found that in normal operation the power control system allows the seventy-five watt halogen lamp to be used about an hour with the compact battery pack shown in the application filed concurrently herewith, and assigned to the same assignee for a portable borescope apparatus and specifically incorporated herein by reference. Obviously, the length of time a particular lamp can be operated will depend in part on the battery pack available, as well as the amount of time that the lamp is turned on to full power.

In prior systems, a mechanical aperture has been used to reduce the light, or the lamp voltage and the lamp current have been limited to reduce light output, but the light has not been turned off for a portion of each cycle as in this system. Thus, the average power consumption of prior systems has been significantly greater. With this system of turning the lamp on and off in accordance with the video signal requirements, very significant amounts of power can be saved and this permits use of a practical battery pack for a borescope instrument.

While this invention has been explained with reference to the embodiment disclosed herein, it is not confined to the details as set forth, and this application is intended to cover any modifications and changes as may come within the scope of the following claims.

What is claimed is:

1. In a borescope/endoscope of the type having an elongated insertion tube with a solid state image sensor in a viewing head at the distal end, a fiber optic cable extending from the distal end to the proximal end, and a control processor module at the proximal end, illumination means comprising:

lamp means operatively positioned adjacent the proximal end of the fiber optic cable for transmitting light therethrough to the object to be viewed;

a source of operating voltage for energizing said lamp means;

control circuit means connected between said lamp means and said operating voltage source;

video signal transmitting means connected between the viewing head and said control circuit means;

said control circuit means being arranged to connect and disconnect said operating voltage and said lamp means at a video frequency rate in accordance with the video signal picked up by said viewing head;

so that as the video signal decreases, the lamp is energized longer and vice-versa.

2. A device as described in claim 1 wherein said fiber optic cable comprises a plurality of optical fibers positioned about the circumference of said insertion tube, and extending from the proximal end to the distal end thereof.

3. A device as described in claim 1 wherein said lamp means comprises a frame member slidably mounted in said control/processor module, lamp socket means fixed on said frame member, and a halogen lamp removably mounted in said socket means so that said lamp means may be conveniently and easily withdrawn from the module and removed for servicing and replacement.

4. A device as described in claim 1 wherein said source of operating voltage is connected to one side of said lamp means and said control circuit means is connected between the other side of said lamp means and the other side of said source of operating voltage to complete a circuit and illuminate the lamp.

5. A device as described in claim 4 wherein said control circuit means includes a power Mosfet connected between one side of said lamp and ground, and said control circuit means is further arranged to turn said power Mosfet on and off in proportion to the magnitude of the video signal picked up by the viewing head.

6. A device as described in claim 5 wherein the duration of each energizing cycle of said lamp means is varied in proportion to the time the video signal picked up by the viewing head of the borescope exceeds a preset value.

7. A device as described in claim 6 wherein as the light picked up by the viewing head increases in intensity, the duration of the energizing of each cycle of operation is reduced.

8. A device as described in claim 1 wherein said control circuit means includes a power Mosfet connected from one side of said lamp means to the operating voltage; means for turning on said power Mosfet at a frequency equal to the video frequencies picked up at the viewing head and means for varying the duration of illumination of said lamp means in each cycle in inverse proportion to the amount of light picked up by the image detector in the viewing head.

9. In a portable battery operated borescope of the type having an elongated insertion tube with a viewing head at the distal end and a fiber optic cable extending from a light source through said insertion tube to the viewing head, the method of controlling the illumination of the object to be viewed which comprises:

connecting one side of a lamp to a power source;

connecting a high speed switching device between the other side of said lamp and ground;

actuating said switch on and off at a video rate in accordance with the video signal picked up at said viewing head; and maintaining said switch in the "on" condition only during the portion of each video cycle that exceeds a preset signal level whereby the power consumption of the illumination is minimized.

* * * * *